United States Patent [19]

Honna et al.

[11] Patent Number: 4,990,691
[45] Date of Patent: Feb. 5, 1991

[54] HIGHER CARBOXYLIC ACID TRIESTER OF ADAMANTANE TRIOL AND LUBRICATING OIL CONTAINING THE SAME

[75] Inventors: Kosaku Honna, Sodegaura; Hiromichi Seiki, Ichihara, both of Japan

[73] Assignee: Idemitsu Kosan Company Limited, Tokyo, Japan

[21] Appl. No.: 482,650

[22] Filed: Feb. 21, 1990

Related U.S. Application Data

[62] Division of Ser. No. 413,537, Sep. 27, 1989, Pat. No. 4,963,792.

[30] Foreign Application Priority Data

Oct. 12, 1988 [JP] Japan .................................. 63-254997
Jan. 26, 1989 [JP] Japan ..................................... 1-17253

[51] Int. Cl.$^5$ ........................ C07C 35/22; C07C 35/00
[52] U.S. Cl. ..................................... 568/818; 568/808
[58] Field of Search ................................ 568/808, 818

[56] References Cited

U.S. PATENT DOCUMENTS

3,342,880 9/1967 Reinhardt ........................... 568/818
3,398,165 8/1968 Duling et al. ....................... 568/818

FOREIGN PATENT DOCUMENTS

0857101 8/1981 U.S.S.R. .............................. 568/818

OTHER PUBLICATIONS

W. H. W. Lunn et al., (1970) pp. 2124–2126 "Functionalization and Cleavage of Adamantane with Lead Tetra–Acetate; the Formation of 2(3–4)abeo–adamantane+from Adamantane" Journal of the Chemical Society.

Primary Examiner—Werren R. Lone
Attorney, Agent, or Firm—Frishauf, Holtz, Goodman & Woodward

[57] ABSTRACT

The novel compound provided by the invention is a higher carboxylic acid triester of adamantane triol such as adamantane-1,3,5-triol tricaprylate not known in the prior art. The compound has a high kinematic viscosity at elevated temperatures despite the low pour point and has high thermal stability in an oxidizing atmosphere so that it is useful as an ingredient of a high-performance lubricating oil.

16 Claims, 3 Drawing Sheets

HIGHER CARBOXYLIC ACID TRIESTER OF ADAMANTANE TRIOL AND LUBRICATING OIL CONTAINING THE SAME

This is a division of application Ser. No. 07/413,537 filed Sept. 27, 1989, now U.S. Pat. No. 4,963,292.

BACKGROUND OF THE INVENTION

1. Field of the Invention

The present invention relates to a higher carboxylic acid triester of adamantane triol as a novel compound and a synthetic lubricating oil containing the same. More particularly, the present invention relates to a higher carboxylic acid triester of adamantane triol which is a novel compound useful as a constituent of high-performance synthetic lubricating oils excellent in both of the low-temperature characteristics and high-temperature characteristics as well as to a high-performance synthetic lubricating oil containing the compound which can be used quite satisfactorily as an engine oil, gear oil, hydraulic working fluid, grease, vacuum pump oil, bearing-impregnating oil, gas turbine oil and the like.

2. Background Information

Synthetic lubricating oils known in the prior art include polyolefins such as oligomers of α-olefin, polyisobutylene and the like, organic ester compounds such as diesters, e.g., di(2-ethylhexyl) sebacate, alkyl esters of pentaerithritol and the like, polyphenyl ethers such as m-bis(m-phenoxyphenoxy) benzene and the like, phosphate esters such as tricresyl phosphate and the like, polyalkylene glycols such as polypropylene glycol and the like, silicone fluids, perfluoroalkyl ethers and so on.

These synthetic lubricating oils have unique characteristics not possessed by any mineral oil-based lubricating oils so that they are used in respective applications in accordance with the particular characteristic properties. It is a trend in the machinery of recent years that the performance of machines is being upgraded increasingly and machines are operated sometimes under extremely adverse conditions so that demand for synthetic lubricating oils is expected to grow more and more; also of concern are the problems of material savings and prevention of environmental pollution. In this regard, active investigations are being carried out to develop a synthetic lubricating oil having further improved characteristics.

Turning now to the derivatives of adamantane or, in particular, ester compounds derived from adamantane, Japanese Patent Publication No. 46-22465 discloses a diester of adamantane-1,3-diol represented by the general formula

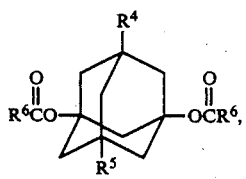

(I)

in which $R^4$ is a hydrogen atom or an alkyl or cycloalkyl group having 1 to 20 carbon atoms and $R^5$ and $R^6$ are each an alkyl or cycloalkyl group having 1 to 20 carbon atoms.

These ester compounds of adamantane, when used as a constituent of a synthetic lubricating oil, have a defect in respect of the viscosity-temperature characteristics although excellent heat resistance can be obtained therewith. For example, a diester of adamantane-1,3-diol, of which the groups denoted by $R^4$ and $R^5$ in the above given general formula (I) are each a methyl group and the group denoted by $R^6$ is an octyl group, has a kinematic viscosity of 7.1 centistokes at 100° C., viscosity index of 95 and pour point of −50° C. or below so that this diester compound could be used as a high-performance synthetic lubricating oil if each of the viscosity at high temperatures and the viscosity index would have a still higher value.

SUMMARY OF THE INVENTION

The present invention accordingly has an object to provide a novel derivative of adamantane useful as a constituent of a high-performance synthetic lubricating oil which is excellent in both of the low temperature characteristics and high temperature characteristics and to provide a synthetic lubricating oil containing the compound Thus, the novel adamantane derivative provided by the present invention is a higher carboxylic acid triester of adamantane triol represented by the general formula

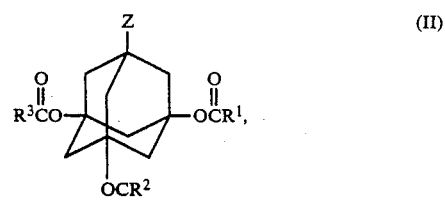

(II)

in which Z is a hydrogen atom or a hydroxyl group and $R^1$, $R^2$ and $R^3$ are each, independently from the others, an alkyl or cycloalkyl group having 4 to 30 carbon atoms.

DETAILED DESCRIPTION OF THE PREFERRED EMBODIMENTS

Figure 1:
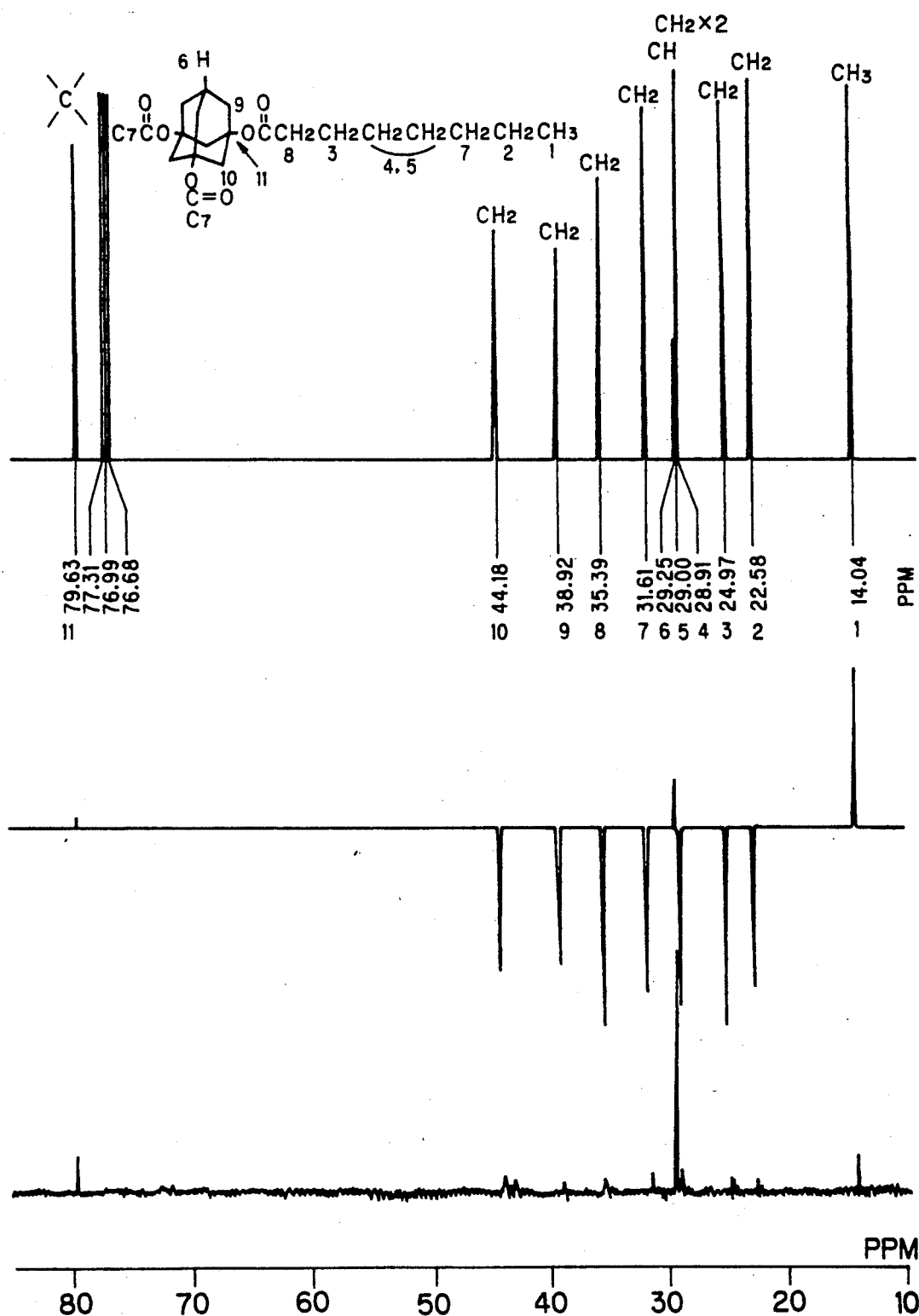
FIGS. 1, 2 and 3 are each a diagram of a $^{13}C$ NMR spectrum, $^1H$ NMR spectrum and infrared absorption spectrum, respectively, of a higher carboxylic triester of adamantane triol according to the present invention.

The higher carboxylic acid triester of adamantane triol represented by the above given general formula (II) is a novel compound not known in the prior art nor described in any literatures. Each of the groups denoted by $R^1$, $R^2$ and $R^3$ in the above given general formula (II) is, independently from the others, an alkyl or cycloalkyl group having 4 to 30 carbon atoms. Although these three groups can be different from each other, it is preferable that all of these groups are of the same kind in view of the higher efficiency in the synthetic preparation of the compound. The symbol Z in the general formula (II) denotes a hydrogen atom or a hydroxyl group.

A higher carboxylic acid triester of adamantane-1,3,5-triol or, namely, a compound of the general formula (II) of which Z is a hydrogen atom can be prepared by the esterification of adamantane-1,3,5-triol with a higher carboxylic acid or a reactive derivative thereof corresponding to the groups denoted by $R^1$, $R^2$ and $R^3$. On the other hand, a higher carboxylic acid triester of 7-hydroxy adamantane-1,3,5-triol or, namely, a compound of the general formula (II) of which Z is a hydroxyl group can be prepared by the esterification of adamantane-1,3,5,7-tetraol with a higher carboxylic acid or a reactive derivative thereof corresponding to $R^1$, $R^2$ and $R^3$.

The above mentioned 1,3,5-triol and 1,3,5,7-tetraol of adamantane can be prepared, according to the reaction scheme A shown below, by oxidizing adamantane (III) into an adamantane diol (IV) which is further oxidized to give adamantane-1,3,5-triol (V) or adamantane-1,3,5,7-tetraol (VI).

REACTION SCHEME A

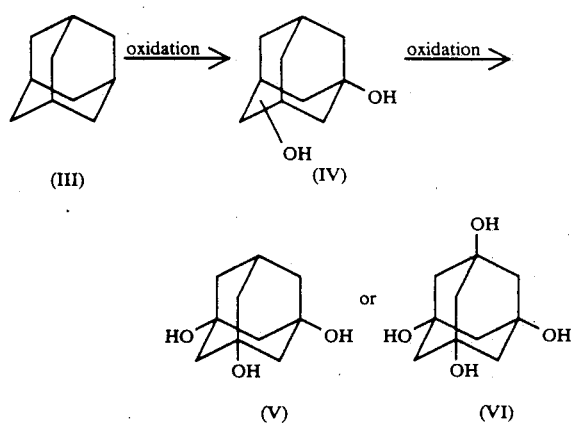

The method for the oxidation of adamantane (III) into the adamantane diol (IV) is not particularly limitative and any of known oxidation methods can be applied thereto. Applicable methods include air oxidation in the presence of a metal salt-based oxidation catalyst and oxidation with chromium trioxide in acetic acid as a solvent, of which the latter method is preferred.

Following is a description of the method for the oxidation of adamantane into an adamantane diol by using chromium as the oxidizing agent. In the first place, adamantane is added to and suspended in acetic acid to give a slurry to which an aqueous solution of chromium trioxide is added dropwise to effect the oxidation reaction. The acetic acid is used in such an amount that the molar ratio of acetic acid to adamantane is preferably in the range from 3 to 7. On the other hand, the chromium trioxide is used in such an amount that the molar ratio thereof to the adamantane is preferably in the range from 4 to 8. When the amount of chromium trioxide is too small, an undesirable result is caused that monools of adamantane are produced in a relatively large amount. When the amount of chromium trioxide is too large, on the other hand, the amount of undesirable by-products is disadvantageously increased. The concentration of chromium trioxide in the aqueous solution should be as high as possible so that the aqueous solution is usually a saturated solution of chromium trioxide.

The oxidation reaction is performed usually at a temperature in the range from 80° to 120° C. When the reaction temperature is too low, the reaction velocity would be impractically low while, when the reaction temperature is too high, undesirable side reactions may take place predominantly. The length of time taken for completion of the oxidation reaction naturally depends on various conditions such as the reaction temperature, amount of chromium trioxide used and the like but the reaction is complete usually within 1 to 20 hours.

After completion of the oxidation reaction, the reaction mixture is usually freed from acetic acid as the solvent by distillation under reduced pressure, neutralized with an alkali and then subjected to extraction of the reaction product by using a suitable organic solvent to give an extract from which the reaction product is isolated by a known method in the form of crude adamantane diol (IV).

The crude adamantane diol obtained in the above described manner can be used usually as such without further purification in the second step oxidation reaction, in which the reaction conditions are about the same as in the above described first step oxidation reaction by using chromium trioxide as the oxidizing agent followed by the post-treatment of the reaction product. The proportion of the yields of adamantane-1,3,5-triol (V) and adamantane-1,3,5,7-tetraol (VI) in the resultant reaction mixture can be controlled by adequately selecting the conditions in the oxidation reaction of the diol with chromium trioxide. The crude reaction product after the above mentioned post-treatment can be esterified as such although it is optional that the crude reaction product is purified by a suitable means to isolate the triol and tetraol in a pure form to be used as the starting material of the esterification reaction.

The adamantane diol (IV) can be prepared by a method other than the direct oxidation of adamantane with chromium trioxide. For example, adamantane is first brominated to give a dibromo adamantane which is reacted with an aqueous solution of silver sulfate and then oxidized with chromium trioxide to give the diol.

Besides the above described reaction scheme A, adamantane-1,3,5-triol and adamantane-1,3,5,7-tetraol can be synthesized via several other synthetic routes, for example, shown by the reaction schemes B and C described below.

REACTION SCHEME B

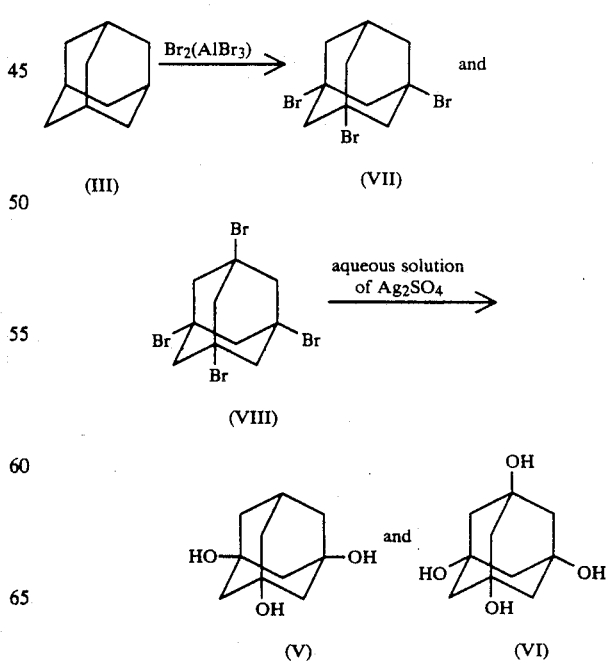

According to this reaction scheme B, adamantane (III) is first brominated with bromine in the presence of aluminum bromide as a catalyst to give 1,3,5-tribromo adamantane (VII) and 1,3,5,7-tetrabromo adamantane (VIII) which are then reacted with an aqueous solution of silver sulfate to give adamantane-1,3,5-triol (V) and adamantane-1,3,5,7-tetraol (VI).

REACTION SCHEME C (AdH is an abridgement for adamantane.)

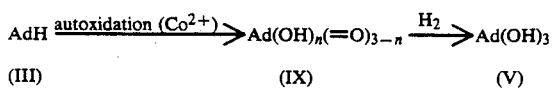

(III)    (IX)    (V)

In the synthetic route according to this reaction scheme C, adamantane (III) is first subjected to autoxidation with air or oxygen to give an adamantane compound (IX) having hydroxyl groups and oxo groups and then the oxo groups are reduced with hydrogen to give adamantane-1,3,5-triol (V).

As a further alternative method, the adamantane triol can be obtained by the hydrolysis of a tribromo adamantane compound in the presence of a tertiary amine compound The tribromo adamantane as the starting material of this method includes 1,3,5-tribromo adamantanes, 1,3,6-tribromo adamantanes, represented by the following general formulas (X) and (XI), respectively, and the like:

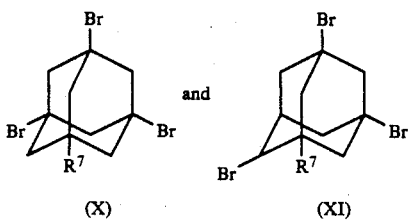

In the above given general formulas (X) and (XI), the symbol $R^7$ denotes a hydrogen atom or a substituent group not inhibitive against the reaction, which is exemplified by lower alkyl groups such as methyl, ethyl, propyl and butyl groups. These tribromo adamantane compounds can easily be obtained, for example, by the bromination of adamantane in the presence of aluminum bromide as a catalyst.

The tribromo adamantane obtained in this method usually contains dibromoadamantane compounds and tetrabromo adamantane compounds as impurities. When an adamantane triol product having a high purity of 95 to 99% is desired, the content of these impurities in the adamantane triol should not exceed 5% by weight or, desirably, 2% by weight.

The tertiary amine compound used in the above mentioned hydrolysis reaction includes trimethyl amine, triethyl amine, 1,8-diazabiscyclo[5.4.0]undecene-7 (DBU), pyridine compounds and the like, of which pyridine compounds are particularly preferred. These tertiary amine compounds can be used either singly or as a combination of two kinds or more according to need.

The above mentioned pyridine compounds include pyridine and substituted pyridines represented by the general formula

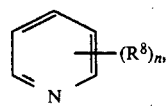

(XII)

in which $R^8$ is a substituent group not inhibitive against the reaction such as lower alkyl groups, e.g., methyl and ethyl groups, di(lower alkyl)-substituted amino groups, e.g., dimethyl amino and diethyl amino groups, and the like and the subscript n is zero or an integer not exceeding 5 while, when n is 2 or larger, each of the groups denoted by $R^8$ can be independent from the others. Particular examples of suitable pyridine compounds include pyridine, α-picoline, β-picoline, γ-picoline, 4-dimethylamino pyridine and the like.

The hydrolysis reaction of the tribromo adamantane is carried out in the presence of one kind or more of these tertiary amine compounds with the addition of water, the amount of which is usually in the range from 10 to 200 moles or, preferably from 20 to 150 moles per mole of the tribromo adamantane. When the amount of water is too small, the adamantane triol as the reaction product cannot be completely dissolved in the reaction mixture to form a slurry-like mixture so that smooth proceeding of the reaction is somewhat disturbed. When the amount of water is too large, on the other hand, the reaction velocity may be disadvantageously decreased due to the decrease in the concentration of the tribromo adamantane as the starting material in the reaction mixture.

On the other hand, the amount of the tertiary amine compound added to the reaction mixture is usually in the range from 5 to 60 moles or, preferably, from 10 to 50 moles per mole of the tribromo adamantine compound. When the amount of the tertiary amine compound is too small, the tribromo adamantane compound cannot be completely dissolved in the reaction mixture to form an inhomogeneous reaction mixture so that smooth proceeding of the reaction is somewhat disturbed. When the amount of the tertiary amine compound is too large, on the other hand, the reaction velocity may be disadvantageously decreased in addition to the economical disadvantage that a large amount of the tertiary amine compound must be recovered from the reaction mixture and recycled.

The hydrolysis reaction is carried out at a temperature, usually, in the range from 150° to 280° C. or, preferably, in the range from 170° to 250° C. When the temperature is too low, the reaction proceeds only in an impractically low conversion. When the reaction temperature is too high, on the other hand, a disadvantage is caused in the decreased yield of the desired reaction product due to the increased formation of tarry matter by the side reactions. The pressure in the reaction is not particularly limitative and the reaction is usually performed under a spontaneously produced pressure at the temperature. The time taken for completion of the reaction naturally depends on various conditions of the reaction such as amount of water added to the reaction mixture, kind and amount of the tertiary amine compound, reaction temperature and so on but the reaction is usually complete within 0.5 to 20 hours. The reaction can be conducted in a batch process, semi-continuous process or continuous process.

In this manner, the tribromo adamantane compound represented by the above given general formula (X) or (XI) is converted into the corresponding adamantane triol compound represented by the general formula

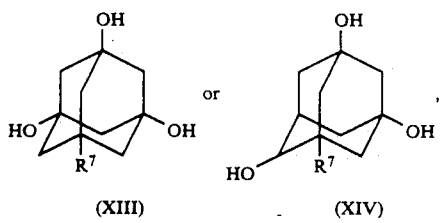

in which $R^7$ has the same meaning as defined before.

The above described hydrolysis reaction to form the adamantane triol compound is usually accompanied by the formation of various by-products including dehydroadamantane diols, dibromo adamantanols, monobromo adamantane diols and the like. The above mentioned dehydroadamantane diols can readily be converted into corresponding adamantane triol compounds when they are heated in an acidic aqueous solution. Further, the amounts of the dibromo adamantanols and monobromo adamantane diols as the by-products can be decreased by appropriately selecting the reaction conditions since these compounds are intermediate products formed in an increased amount when the reaction is performed under mild reaction conditions.

The reaction mixture after completion of the above described hydrolysis reaction is then subjected to a post-treatment preferably in the following manner. Thus, the reaction mixture after completion of the hydrolysis reaction is admixed with an alkali metal hydroxide such as sodium hydroxide and potassium hydroxide with an object that, since a part of the tertiary amine compound in the reaction mixture is contained in the mixture in the form of a pyridinium salt with the hydrogen bromide produced by the reaction, the pyridinium salt of the amine compound is decomposed to isolate the amine compound in the free form. Thereafter, the reaction mixture is distilled to remove the thus isolated tertiary amine compound and water. The residue of distillation is then admixed with diluted sulfuric acid of a concentration of about 3 to 10% by weight and heated at a temperature, usually, in the range from 50° to 100° C. to effect hydration of the dehydroadamantane diols as the by-products followed by neutralization with an alkali. The unreacted tribromo adamantane compounds are removed from the mixture by a suitable means such as filtration. The filtrate after removal of the unreacted tribromo adamantanes is distilled to remove water and the residue after distillation is subjected to extraction with an organic solvent such as lower alcohols to give an extract from which the organic solvent is removed by distillation so that the desired product of the adamantane triols can be obtained as a residue in a crystalline form. The unreacted tribromo adamantanes recovered above can be recycled as such to the step of hydrolysis. The recycled amount is usually in the range from 2 to 30% by weight based on the overall amount of the charged starting material. The adamantane triol compounds can be used satisfactorily not only as the intermediate material for the preparation of the triester compounds useful as a high-performance synthetic lubricating oil but also as an intermediate for the synthetic preparation of various kinds of industrially important organic chemicals.

The adamantane-1,3,5-triol (V) obtained in this manner as well as the adamantane triol derivatives of the formulas (XIII) and (XIV), in which $R^7$ is a hydrogen atom or a substituent group, and adamantane-1,3,5,7-tetraol (VI) can be esterified with a higher carboxylic acid or a reactive derivative thereof to give a higher carboxylic acid triester of adamantane-1,3,5-triol and a higher carboxylic acid triester of 7-hydroxy adamantane-1,3,5-triol, respectively. The higher carboxylic acid used in the esterification of the adamantane triols and tetraols is represented by the general formula R—CO—OH, in which R is an alkyl group or cycloalkyl group having 4 to 30 carbon atoms. Particular examples of the higher carboxylic acid include caproic acid, isovaleric acid, n-heptanoic acid, caprylic acid, pelargonic acid, capric acid, n-undecylic acid, lauric acid, myristic acid, palmitic acid, stearic acid, eicosanoic acid, behenic acid, cyclohexane carboxylic acid, decahydronaphthalene carboxylic acid and the like. The reactive derivatives of the above mentioned higher carboxylic acid include lower alkyl esters, acid chlorides, acid anhydrides and the like of the acid.

The esterification reaction is performed usually by using from 3 to 6 moles of the above mentioned higher carboxylic acid or a reactive derivative thereof per mole of the adamantane triol compound, e.g., adamantane-1,3,5-triol, or adamantane-1,3,5,7-tetraol. When the amount of the higher carboxylic acid or a reactive derivative thereof is too small, the relative amount of the monoester and diester as the undesirable by-products is naturally increased while no particular additional advantages can be obtained by increasing the amount of the higher carboxylic acid or a reactive derivative thereof over the above mentioned upper limit. The esterification reaction is carried out usually at a temperature in the range from 50 to 150° C. When the reaction temperature is too low, the reaction velocity is impractically low while an excessively high reaction temperature may result in predominance of undesirable side reactions.

The reaction mixture after completion of the esterification reaction is processed according to a conventional procedure to isolate higher carboxylic acid triesters of adamantane triol compounds of the present invention represented by the general formula

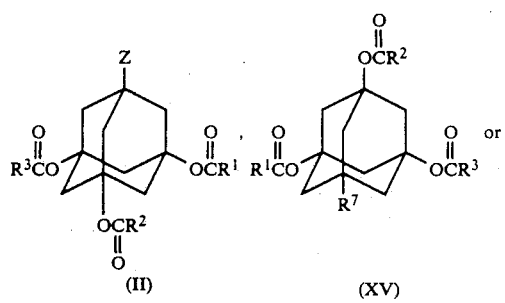

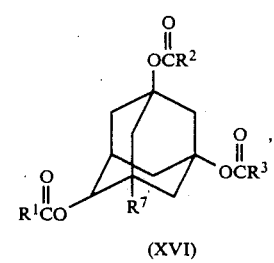

in which $R^1$, $R^2$, $R^7$ and Z each have the same meaning as defined before. These compounds are each a novel compound not described in any prior art literatures and have the properties to be an excellent lubricating oil. For example, adamantane-1,3,5-triol tricaprylate, which is a compound expressed by the above given general formula (II) in which $R^1$, $R^2$ and $R^3$ are each a n-heptyl group and Z is a hydrogen atom, has properties shown in Table 1 below and is highly heat resistant and excellent in both of the low temperature characteristics and high temperature characteristics as a synthetic lubricating oil with a high kinematic viscosity even at high temperatures despite the low pour point as compared with adamantane diol dicaprylate and adamantane monool monocaprylate.

pletely replaced with nitrogen gas by repeating evacuation and introduction of nitrogen gas.

The reaction mixture in the autoclave was heated up to a temperature of 250° C. under agitation and kept at this temperature for 5 hours to effect the hydrolysis reaction. After the end of the reaction time, the autoclave was cooled to room temperature and the reaction mixture taken out of the autoclave was admixed with 1.6 g (0.0402 mole) of sodium hydroxide to decompose the pyridinium salt. Thereafter, the reaction mixture was freed from pyridine and water by distillation to leave a residue which could be identified by the gas chromatographic analysis (FID-OV-101) to be a mixture composed of 41% by weight of adamantane-1,3,5-triol, referred to as 1,3,5-Ad(OH)$_3$, 36% by weight of

TABLE 1

| Compound | Adamantane-1,3,5-triol tricaprylate | Adamantane-1,5-diol dicaprylate | Adamantane monool monocaprylate |
|---|---|---|---|
| Structural formula | (structure with $H_{15}C_7CO$–, –$OCC_7H_{15}$, $OCC_7H_{15}$) | (structure with –$OCC_7H_{15}$, $OCC_7H_{15}$) | (structure with –$OCC_7H_{15}$) |
| Molecular weight | 562 | 420 | 277 |
| Kinematic viscosity | | | |
| 40° C., cSt | 72.87 | 32.44 | 12.97 |
| 100° C., cSt | 9.55 | 5.57 | 3.08 |
| Viscosity index | 109 | 109 | 93 |
| Density at 15° C., g/cm$^3$ | 1.005 | 0.997 | 0.9896 |
| Pour point, °C. | −50.0> | −42.5 | −50.0> |
| Differential thermal analysis | | | |
| Temperature for 50% weight loss in N$_2$, °C. | 345 | 295 | 222 |
| Temperature for exothermic peak in air, °C. | 331 | 313 | 223 |

As is understood from the data given in Table 1, the higher carboxylic acid triester of adamantane triol according to the present invention is excellent in both of the low temperature characteristics and high temperature characteristics so that it is useful as a high-performance synthetic lubricating oil.

When the higher carboxylic acid triesters of adamantane triol are used as a synthetic lubricating oil, it is optional that the lubricating oil is formulated either with a single kind of the triesters or with two kinds or more thereof in combination. It is further optional that one kind or more of the higher carboxylic acid triesters of adamantane-1,3,5-triol are combined with one kind or more of higher carboxylic acid triesters of 7-hydroxyadamantane-1,3,5-triol derived from adamantane-1,3,5,7-tetraol.

In the following, examples are given to illustrate the higher carboxylic acid triesters of adamantane triols according to the present invention in more detail but not to limit the scope of the invention in any way.

PREPARATION EXAMPLE 1

Into an autoclave of 100 ml capacity were introduced 5.0 g (0.0134 mole) of 1,3,5-tribromo adamantane, referred to as AdBr$_3$, 18 g (1 mole) of water and 49.2 g (50 ml) of pyridine and, after evacuation down to a pressure of about 20 mmHg, nitrogen gas was introduced into the autoclave. The air inside the autoclave was comdehydroadamantane diols, referred to as DHAd(OH)$_2$, 10% by weight of monobromo adamantane diol, referred to as Ad(OH)$_2$Br, and 9% by weight of others.

The residue was admixed with 200 ml of sulfuric acid of 5% by weight concentration and agitated for 30 minutes at 80° C. followed by neutralization with sodium hydroxide and removal of the suspended matter by filtration. The filtrate was subjected to evaporation of water to dryness on a rotary evaporator to give a crystalline mixture composed of Ad(OH)$_3$, sodium bromide and sodium sulfate.

In the next step, the thus obtained crystalline mixture was admixed with 50 ml of ethyl alcohol and agitated for 30 minutes followed by filtration to give an ethyl alcohol extract as the filtrate. The residue was further subjected to extraction with ethyl alcohol in the same manner. After three times extraction treatments in this manner, the ethyl alcohol extracts were combined and subjected to evaporation of ethyl alcohol to dryness on a rotary evaporator to give 2.3 g of a light yellow crystalline product.

The result of a gas chromatographic analysis (OV-101) indicated that this crystalline product contained 93% by weight of 1,3,5-Ad(OH)$_3$, which could be identified by the mass spectrometric analysis, $^1$H-NMR analysis and $^{13}$C NMR analysis. Table 2 below summarizes some of the experimental data for this synthetic preparation.

COMPARATIVE EXAMPLE 1

The same experimental procedure as in Preparation Example 1 described above was repeated except that pyridine was replaced with silver sulfate and sulfuric acid in amounts indicated in Table 2 below, the amount of water added to the reaction mixture was 8.5 g, the reaction temperature was 100° C. and the reaction time was one hour. The experimental data of the same items as in Preparation Example 1 are shown in Table 2.

TABLE 2

|  | Preparation Example 1 | Comparative Example 1 |
|---|---|---|
| Amount charged, g |  |  |
| AdBr$_3$ | 5.0 | 5.0 |
| water | 18.0 | 8.5 |
| additives | pyridine 49.2 | Ag$_2$SO$_4$ 8.35 H$_2$SO$_4$ 45.8 |
| Molar ratio of water: AdBr$_3$ | 75 | 35 |
| Molar ratio of additive: AdBr$_3$ | 46 | Ag$^+$/AdBr$_3$ 4 |
| Reaction conditions |  |  |
| temperature, °C. | 250 | 100 |
| time, hours | 5 | 1 |
| Conversion of AdBr$_3$, % | 94 | 99 |
| Selectivity, % |  |  |
| 1,3,5-Ad (OH)$_3$ | 93 | 76 |
| DHAd (OH)$_2$ | 1 | — |
| others | 6 | 23 |
| Yield of Ad (OH)$_3$, % | 87 | 75 |

EXAMPLE 1

(1) Preparation of Adamantane Triol by Oxidation of Adamantane

Into a four-necked flask of 2 liter capacity were introduced 200 g (1.47 moles) of adamantane, referred to as AdH, and 1500 g of acetic acid to form a slurried reaction mixture which was agitated at 80° C. An aqueous solution of chromic acid prepared by dissolving 736 g (7.36 moles) of chromium trioxide in 400 ml of water was added dropwise to the reaction mixture in the flask under agitation gradually in such a rate that the temperature of the reaction mixture did not exceed 120° C. by the heat of exothermic reaction.

After the end of the dropwise addition of the chromic acid solution, the reaction mixture was further agitated at 100° C. for additional one hour followed by removal of most part of water and acetic acid by evaporation on a rotary evaporator. Thereafter, the residue after evaporation was dissolved by adding about 1 liter of deionized water to give an aqueous solution which was neutralized to have a pH of 7 by adding a small amount of sodium hydroxide solid. The thus neutralized solution was subjected to evaporation of water on a rotary evaporator until the whole volume thereof was reduced to about 1 liter.

In the next place, 1 liter of ethyl acetate was added to the thus concentrated aqueous solution to extract the reaction product at 70° C. This extraction treatment was repeated five times and the extract solution as combined was freed from ethyl acetate by distillation to leave 130 g of a white crystalline product which contained 90% by weight of adamantane diol. The yield was 65% by weight of the starting adamantane. The above described procedure was repeated so as to prepare crude adamantane diol in an amount sufficient for the preparation of adamantane triol in the succeeding step.

In the next place, 200 g (about 1.2 moles) of the thus obtained crude adamantane diol and 1420 g of acetic acid were introduced into a four-necked flask of 2 liter capacity to form a slurried mixture An aqueous solution of chromic acid prepared by dissolving 480 g of chromium trioxide in 240 ml of water was added dropwise gradually to the slurried mixture in the flask kept at 90° C. under agitation to effect the reaction which was less exothermic than the reaction in the preceding step. .

After completion of the dropwise addition of the chromic acid solution, the reaction mixture in the flask was agitated for an additional two hours at 90° C. and subjected to evaporation to remove most of the water and acetic acid therefrom on a rotary evaporator. Thereafter, the residue after evaporation was admixed with about 1 liter of water and neutralized with sodium hydroxide to have a pH of 7 in the same manner as before.

The thus neutralized reaction mixture was subjected to evaporation of water on a rotary evaporator to give a concentrated solution which was subjected to extraction with ethyl acetate in the same manner as above to give 120 g of a white crystalline product which was crude adamantane triol. The yield was 60% of the amount of the starting adamantane diol. The result of the gas chromatographic analysis (OV-101) indicated that this crude product contained 85% by weight of adamantane triol. The crude adamantane triol could be purified by recrystallization from ethyl alcohol to give a purified product of adamantane triol having a purity of 98% by weight

(2) Preparation of Adamantane Triol Tricaprylate

Into 316 g (1.95 moles) of caprylic chloride (reagent grade, a product by Tokyo Kasei Co.) taken in a four-necked flask of 1 liter capacity and heated at 90° C. under a stream of nitrogen gas with agitation were added 80 g (0.43 mole) of the above obtained adamantane triol. Hydrogen chloride gas was evolved from the reaction mixture which was further agitated for 1 hour with the temperature increased to 140° C.

After completion of the reaction carried out in this manner, the reaction mixture was admixed with 500 ml of hexane and an aqueous solution prepared by dissolving 200 g of sodium hydrogen carbonate in 2 liters of water and the mixture was agitated for 24 hours at room temperature. The mixture was kept standing to be separated into two layers and subjected to phase separation to discard the aqueous alkaline solution. The organic solution was washed twice with water and then dried over anhydrous sodium sulfate followed by removal of hexane by distillation. Further, the product was subjected to distillation under the conditions of a reduced pressure of 1 mmHg and a bottom temperature of 210° C. to remove the acid chloride remaining in the mixture in a trace amount so that a liquid product in an amount of 240 g was obtained as the distillation residue. The yield was 98% of the theoretical value.

Figure 2:
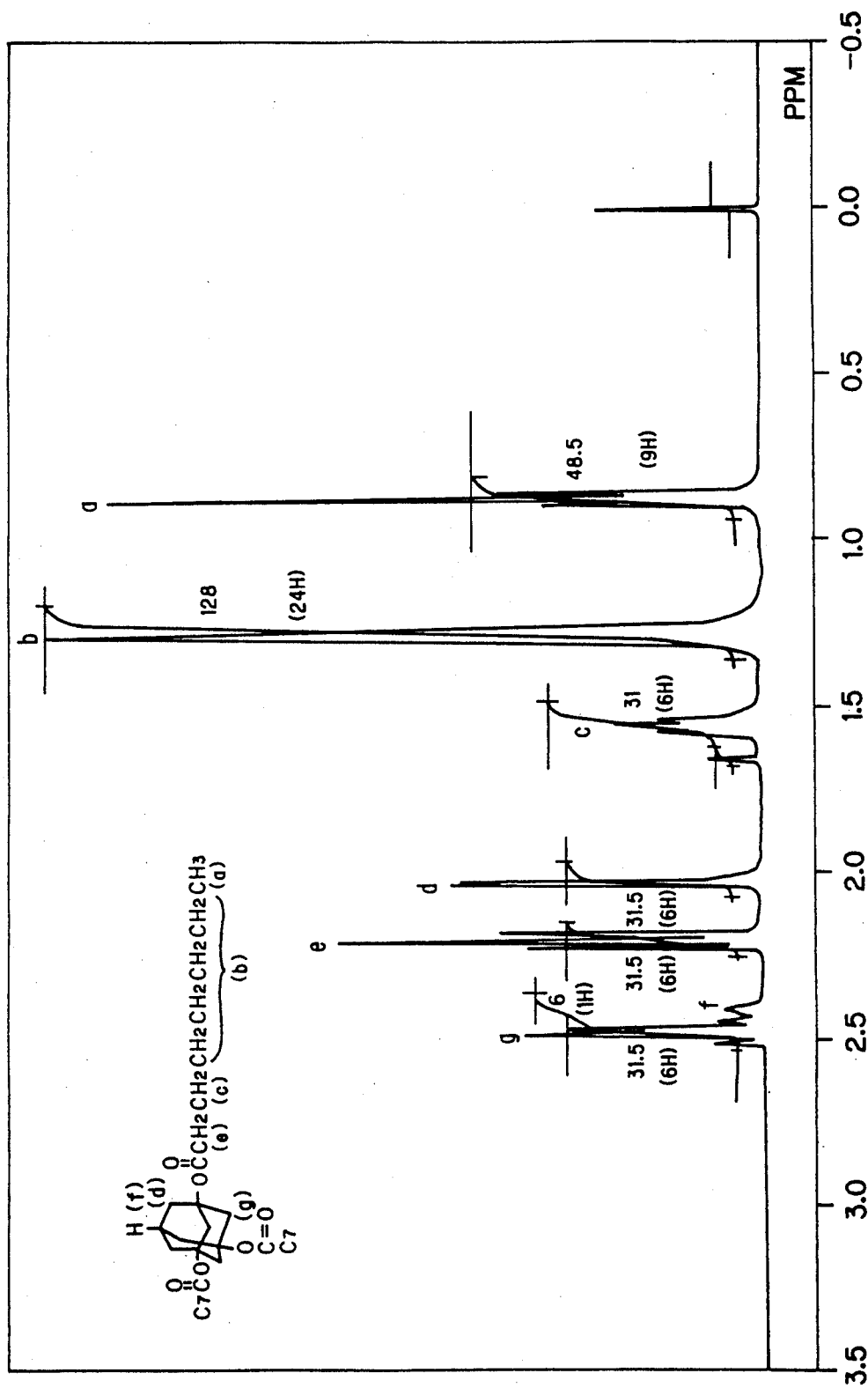
Figure 3:
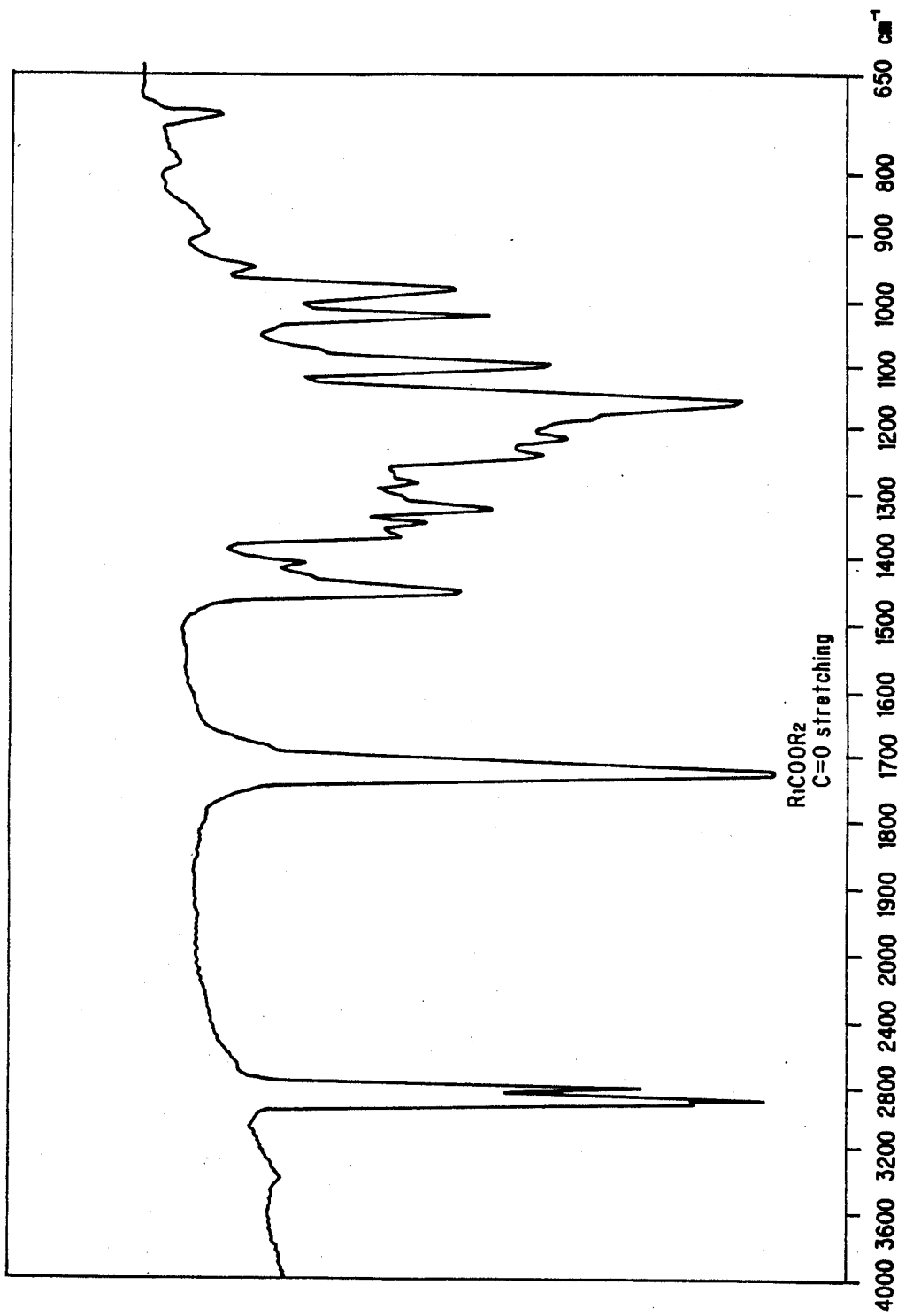

FIGS. 1, 2 and 3 of the accompanying drawing each show a diagram of $^{13}$C NMR spectrum, $^1$H NMR spectrum and infrared absorption spectrum, respectively, of the thus obtained liquid product. A strong absorption band is noted at a wave number of 1725 cm$^{-1}$ in the infrared absorption spectrum, which is assignable to the stretching vibration of the carbonyl groups. The results of the elementary analysis of this product were: C 72.2%; H 10.4%; and O 16.7%, as found (C 72.6%; H 10.3%; and O 17.1%, as calculated for C$_{34}$H$_{58}$O$_6$).

These analytical results supported the conclusion that this liquid product was adamantane-1,3,5-triol tricaprylate expressed by the structural formula:

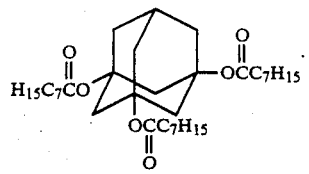

(3) Properties of Adamantane-1,3,5-triol Tricaprylate

Table 1 shown above summarizes several parameters for the primary evaluation of the thus obtained adamantane-1,3,5-triol tricaprylate, as a lubricating oil, together with the corresponding properties of adamantane-1,5-diol dicaprylate, and adamantane monool caprylate.

It can be concluded from the data shown in Table 1 that the adamantane-1,3,5-triol tricaprylate according to the present invention has following characteristics.

(1) The compound has a high kinematic viscosity of 9.55 centistokes at 100° C. despite the low pour point of −50° C. or below.

It is known that a compound having a pour point of −50° C. or below has a kinematic viscosity at 100° C. of 4 to 5 centistokes, as is the case in trimethylol propane tricaprylate, from the general relationship between the pour point and the kinematic viscosity at 100° C. in hindered ester compounds having excellent heat resistance. Apart from such a general relationship, the adamantane-1,3,5-triol tricaprylate according to the present invention has a kinematic viscosity at 100° C. larger by about 5 to 6 centistokes than the above mentioned conventional compound. This property is very important for a synthetic lubricating oil. Namely, a synthetic lubricating oil having a low pour point but high kinematic viscosity at elevated temperatures can be used in an ambience of very low temperature of, for example, −53° C. or below, which is the pour point required for a jet engine oil, while an oil film having a sufficiently large thickness can be obtained on a surface lubricated with the lubricating oil even at high temperatures.

(2) The compound is characterized by a very high thermal stability. As is understood from the temperature of the exothermic peak in the differential thermal analysis in an air stream, it is apparent that the adamantane-1,3,5-triol tricaprylate according to the present invention has very high thermal stability in an oxidizing atmosphere as compared with adamantane diol dicaprylate and adamantane monool caprylate.

To summarize the advantages of the present invention, the higher carboxylic acid triester of adamantane triol according to the present invention, which is a novel compound not described in any prior art literature, has excellent thermal stability and, despite the low pour point, has a high kinematic viscosity at high temperatures so that it is useful as a high-performance lubricating oil which is required to be excellent in both of the low-temperature characteristics and high-temperature characteristics.

The synthetic lubricating oil of the present invention, of which the principal ingredient is the higher carboxylic acid triester of adamantane triol, has excellent characteristics mentioned above so that it can be used quite satisfactorily, for example, as an engine oil, gear oil, hydraulic working fluid, grease, vacuum pump oil, bearing-impregnating oil, gas turbine oil and the like.

What is claimed is:

1. A process for producing an adamantane triol which comprises hydrolyzing a tribromoadamantane compound in the presence of a pyridine compound.

2. The process as claimed in claim 1, wherein the tribromo adamantane compound is 1,3,5-tribromoadamantane of the formula

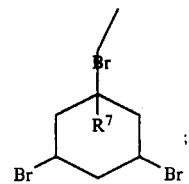

1,3,6-tribromoadamantane of the formula

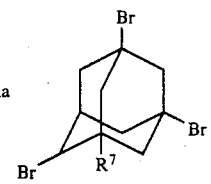

or mixtures thereof, wherein $R^7$ is a hydrogen atom or a lower alkyl group.

3. The process as claimed in claim 2, wherein $R^7$ is selected from the group consisting of methyl, ethyl, propyl and butyl.

4. The process as claimed in claim 1, wherein said hydrolyzing is conducted with water in an amount of 10 to 200 moles per mole of the tribromoadamantane compound.

5. The process as claimed in claim 2, wherein said hydrolyzing is conducted with water in an amount of 20 to 150 moles per mole of the tribromoadamantane compound.

6. The process as claimed in claim 1, wherein the amount of the pyridine compound is 5 to 60 moles per mole of the tribromo adamantane compound.

7. The process as claimed in claim 5, wherein the amount of pyridine compound added is 10 to 50 moles per mole of the tribromo adamantane compound.

8. The process as claimed in claim 1, wherein the hydrolyzing is carried out at a temperature of 150 to 280° C.

9. The process as claimed in claim 7, wherein the hydrolyzing is carried out at a temperature of 170° to 250 ° C.

10. The process as claimed in claim 1, wherein the hydrolyzing is carried out for 0.5 to 20 hours.

11. The process as claimed in claim 1, wherein the pyridine compound is of the formula

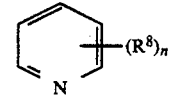

wherein $R^8$ is a lower alkyl group or a di(lower alkyl)-substituted amino group and n is zero or an integer not exceeding 5 and when n is 2 or larger, the groups represented by $R^8$ can be different from each other.

12. The process as claimed in claim 11, wherein $R^8$ is selected from the group consisting of methyl, ethyl, dimethyl amino and diethyl amino.

13. The process as claimed in claim 1, wherein the pyridine compound is selected from the group consisting of pyridine, α-picoline, β-picoline, γ-picoline and 4-dimethylamino pyridine.

14. The process as claimed in claim 1, wherein the pyridine compound is pyridine.

15. The process as claimed in claim 4, wherein the amount of the pyridine is 5 to 60 moles per mole of the tribromo adamantane and the hydrolyzing is conducted at 150 to 280° C. for 0.5 to 20 hours.

16. A process for producing an adamantane triol which comprises conducting a hydrolysis of a reaction mixture which consists essentially of water, a tribromoadamantane compound selected from the group consisting of 1,3,5-tribromoadamantane and 1,3,6-tribromoadamantane and pyridine, wherein the amount of water is 10 to 200 moles per mole of the tribromo adamantane, the amount of the pyridine is 5 to 60 moles per mole of the tribromo adamantane and the hydrolysis is conducted at a temperature of 150° to 280° C. for 0.5 to 20 hours.

* * * * *